United States Patent [19]

Sauer et al.

[11] Patent Number: 4,851,435
[45] Date of Patent: Jul. 25, 1989

[54] ANTIVIRAL AND ANTITUMOR XANTHATE PHARMACEUTICAL COMPOSITIONS

[75] Inventors: Gerhard Sauer; Eberhard Amtmann, both of Heidelberg; Klaus W. Hummel, Frankfurt, all of Fed. Rep. of Germany

[73] Assignee: Merz +Co. GmbH & Co., Frankfurt, Fed. Rep. of Germany

[21] Appl. No.: 892,346

[22] Filed: Aug. 1, 1986

[30] Foreign Application Priority Data

Aug. 2, 1985 [DE] Fed. Rep. of Germany ....... 3527871
Jun. 23, 1986 [DE] Fed. Rep. of Germany ....... 3620939

[51] Int. Cl.$^4$ ................ A61K 31/265; A61K 31/445
[52] U.S. Cl. .................................... 514/512; 514/305; 514/345; 514/351; 514/471; 514/473
[58] Field of Search ............... 514/512, 471, 473, 345, 514/351, 305

[56] References Cited

U.S. PATENT DOCUMENTS 4,602,037 7/1986 Scherm et al. ...................... 514/512

FOREIGN PATENT DOCUMENTS 1174978 9/1984 Canada .
1175047 9/1984 Canada .
2554428 6/1976 Fed. Rep. of Germany .
3146772 9/1982 Fed. Rep. of Germany .
2091244 6/1982 United Kingdom .
2103089 2/1983 United Kingdom .

OTHER PUBLICATIONS

*Chemical Abstract*, 80:66926q (1974) [Stelzl, G. et al., *Arzneim-Forsch;* 1973, 23(10), 1470-3].
*Chemical Abstracts*, 84:69722p (1976) [Iwata, K. et al., *Proc. Int. Congr. Chemother.*, 8th 1973, 1,945-7].
*Chemical Abstracts*, 87:194677z (1977) [Iwata, K. et al., *Antimicrob. Agents Chemother.*, 1977, 12(2), 206-12].
*Chemical Abstracts*, 90:67131v (1979) [Sameb, S. et al., *Can. J. Microbiol.* 1978, 24(11), 1321-30].
*Chemical Abstracts*, 90:98047b (1979) [Swiss 604, 523, Polony et al., 9/15/78].
*Chemical Abstracts*, 103:159038k (1985) [Viegas, C. et al., *Biotechnol. Lett.* 1985, 7(6), 611-14].
J. Sands et al., *Antimicrobial Agents and Chemotherapy*, vol. 15, No. 1, pp. 134-136 (Jan. 1979).

*Primary Examiner*—Richard A. Schwartz
*Attorney, Agent, or Firm*—Gordon W. Hueschen

[57] ABSTRACT

The invention refers to antiviral and antitumor compositions which are useful for the control of viruses and tumors and which, in addition to a known antiviral or antitumor active xanthate, contain an adjuvant which increases its antiviral and antitumor action. The adjuvant is an ionic, preferably an anionic, compound with a lipophilic group and a hydrophilic group, preferably an alkali metal deoxycholate or a compound the lipophilic moiety of which is a straight or branched, saturated or unsaturated, aliphatic group with six to eighteen carbon atoms, and the hydrophilic group of which has one or two carboxyl, sulphate, sulphonate, or phosphate groups, or a pharmaceutically-acceptable salt thereof.

24 Claims, 3 Drawing Sheets

ANTIVIRAL AND ANTITUMOR XANTHATE PHARMACEUTICAL COMPOSITIONS

The present invention relates to novel compositions suitable for use in combating viruses and tumors, i.e., in the elimination, amelioration, palliation, or alleviation of viruses and tumors and conditions resulting therefrom, e.g., afflictions, infections, or diseases, which compositions, in addition to a known antiviral and antitumor-active xanthate compound, contain an ionic adjuvant compound, having both a lipophilic and a hydrophilic group, which enhances or increases the antiviral and antitumor action thereof.

In the Deutsche Offenlegungsschrift (published German patent application) 31 46 772, as well as in UK Pat. No. 2,091,244, Canadian Pat. Nos. 1,174,978 and 1,175,047, and U.S. Pat. No. 4,602,037, issued July 22, 1986, there are described xanthates which have interesting pharmacological properties, particularly antiviral and antitumor activity or effect.

It has now been found that certain adjuvants, which by themselves do not exhibit antiviral or antitumor activity, improve the action of antiviral and antitumor xanthates, especially those described in the Deutsche Offenlegungsschrift 31 46 772 of Sept. 2, 1982, the UK Pat. No. 2091244 published July 28, 1982 and granted Feb. 6, 1985, the Canadian Pat. Nos. 1,174,978 and 1,175,047, both of Sept. 25, 1984, and the aforesaid U.S. Pat.

The invention therefore relates to antiviral and antitumor compositions which are useful for the alleviation of virus and tumor conditions and which contain, as active substance, a known antiviral and antitumor xanthate compound, especially one falling within the scope of formula I:

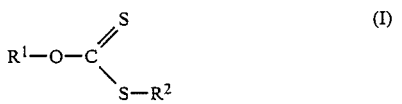

wherein $R^1$ represents norbornyl, tricyclodecyl (including adamantyl), benzyl, straight or branched $C_3$–$C_{20}$-alkyl, $C_3$–$C_{20}$-cycloalkyl, furyl, pyridyl, or quinuclidinyl or the aforesaid straight or branched $C_3$–$C_{20}$-alkyl optionally substituted by hydroxy or $C_1$–$C_4$-alkoxy, or by halogen or the aforesaid $C_3$–$C_{20}$-cycloalkyl optionally substituted by hydroxy, $C_1$–$C_4$-alkoxy, $C_1$–$C_4$-alkyl, or halogen, and wherein $R^2$ represents a monovalent or multivalent metal atom, straight or branched $C_1$–$C_6$-alkyl, which may optionally be substituted by hydroxy, $C_1$–$C_4$-alkoxy, amino, $C_1$–$C_4$-alkylamino, ($C_1$–$C_4$-alkyl)$_2$-amino, ($C_1$–$C_4$-alkyl)$_3$-ammonium, or halogen, or 2,3-dihydroxypropyl or $\omega$-hydroxy-($C_1$–$C_4$-alkoxy)-methyl, and which are characterized in that they contain at least one ionic adjuvant compound having both a lipophilic and a hydrophilic group.

These two ingredients are essential according to the invention and the compositions of the invention accordingly comprise or "consist essentially" of these two ingredients.

The ionic adjuvant or "action-increasing" compound, having both lipophilic and hydrophilic groups, is preferably a compound, the lipophilic group of which is a straight or branched aliphatic group with 6 to 18 carbon atoms, inclusive, whereas the hydrophilic group preferably comprises 1 or 2 carboxyl and/or 1 or 2 sulphate, sulphonate, or phosphate groups. Advantageously the compound is an aliphatic mono or dicarboxylic acid with 6 to 18 carbon atoms, inclusive, or a mono or disulphate, mono or disulphonate, or mono or diphosphate compound having the same number of carbon atoms, which may also comprise 1 or 2 ether and/or amide groups. Also suitable are aliphatic monocarboxylic acids with 9 to 13 carbon atoms, inclusive, as well as fatty alcohol sulphates, fatty alcohol ether sulphates, fatty alcohol phosphates, fatty alcohol ether phosphates, alkane sulphonates, olefinic sulphonates, sulphocarboxylic acid esters, and glyceride sulphates, in each case having 8 to 18 carbon atoms, inclusive. Steroid acids such as deoxycholic acid may advantageously be employed, preferably in the form of an alkali metal salt thereof, e.g., the sodium or potassium salt. Particularly advantageous are naturally-occurring fatty acids or fatty alcohol sulphates having 8 to 18, especially 8 to 14, and even more especially 10 to 12, carbon atoms inclusive. Eleven carbon atoms appears to be the optimum number in this series. In general, the adjuvant compound may advantageously contain from about eight to about twenty-four, preferably eight to fourteen, carbon atoms inclusive, is preferably anionic, and is advantageously employed in the form of a pharmaceutically-acceptable salt thereof, e.g., an alkali metal salt such as the sodium or potassium salt thereof.

OBJECTS OF INVENTION

Figure 1:
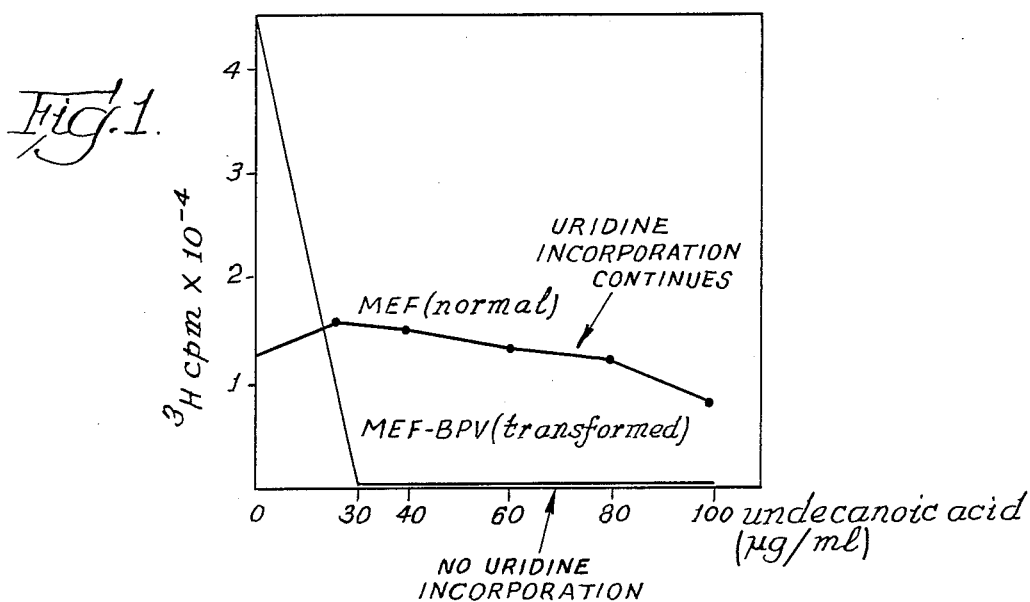
FIG. 1 is a graph depicting the uptake of radioactive uridine in transformed and nontransformed (normal) mouse embryo fibroblast cells with various combinations of active ingredient (D609) and adjuvant in which the amount of active ingredient is fixed at $20\mu g/ml$ and the amount of adjuvant is varied between 10 and $100\mu g/ml$.

To provide an antiviral and antitumor composition comprising a known antiviral and antitumor active xanthate compound and an activity-enhancing amount of an ionic adjuvant compound having both a lipophilic and a hydrophilic moiety, which adjuvant also extends the effect of the antiviral and antitumor xanthate over a broader pH range, including the physiological pH range; a method for the preparation of such a composition; the use of such a composition in antiviral or antitumor therapy, and a method of combating a virus or tumor which comprises concurrently administering to a subject or situs afflicted with a virus or tumor an amount of an antiviral and antitumor xanthate together with an activity-enhancing amount of an ionic adjuvant containing both a lipophilic and hydrophilic group, which combined amounts are effective for such antiviral or antitumor purpose, either individually or in the form of a unitary composition containing the same. Other objects will become apparent hereinafter, and still other objects will be obvious to one skilled in the art.

SUMMARY OF INVENTION

What we therefore consider and believe to be our invention, inter alia, comprises the following:

An antiviral and antitumor composition comprising (a) an antiviral and antitumor xanthate and (b) an ionic adjuvant compound containing both a lipophilic group and a hydrophilic group; such composition wherein the xanthate (a) has the formula I:

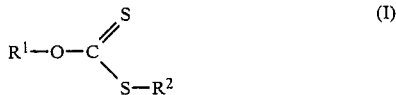

wherein

R¹ represents norbornyl, tricyclodecyl, benzyl, $C_3-C_{20}$-alkyl, $C_3-C_{20}$-cycloalkyl, furyl, pyridyl, quinuclidinyl; $C_3-C_{20}$-alkyl substituted by hydroxy, $C_1-C_4$-alkoxy, or halogen; or $C_3-C_{20}$-cycloalkyl substituted by hydroxy, $C_1-C_4$-alkoxy, $C_1-C_4$-alkyl, or halogen; and R² represents a monovalent or multivalent metal atom, $C_1-C_6$-alkyl, $C_1-C_6$-alkyl substituted by hydroxy, $C_1-C_4$-alkoxy, amino, $C_1-C_4$-alkylamino, $(C_1-C_4$-alkyl$)_2$-amino, $(C_1-C_4$-alkyl$)_3$-ammonium, or halogen; or 2,3-dihydroxypropyl or ω-hydroxy-$(C_1-C_4$-alkoxy)-methyl; such composition wherein the adjuvant compound is one in which the lipophilic group comprises an aliphatic group with six to eighteen carbon atoms, inclusive, and the hydrophilic group comprises one or two carboxyl, sulphate, sulphonate, or phosphate groups, or a pharmaceutically-acceptable salt thereof; such composition wherein the adjuvant compound is an aliphatic mono or dicarboxylic acid, or such an acid which is fluorinated, or an aliphatic mono or disulphate, mono or disulphonate, or mono or diphosphate, in any event having six to eighteen carbon atoms, inclusive, or such a compound having one or two ether or amide groups, or a pharmaceutically-acceptable salt thereof; such composition wherein the adjuvant compound is an aliphatic monocarboxylic acid with nine to twelve carbon atoms, inclusive, or such an acid which is fluorinated, or a pharmaceutically-acceptable salt thereof, or an eight to eighteen carbon atom inclusive fatty alcohol sulphate, fatty alcohol phosphate, fatty alcohol ether phosphate, fatty alcohol ether sulphate, alkane sulphonate, olefinic sulphonate, sulphocarboxylic acid ester or glyceride sulphate, or a pharmaceutically-acceptable salt thereof; such composition wherein the adjuvant compound is a naturally-occurring fatty acid or a fatty alcohol sulphate with about eight to eighteen carbon atoms, inclusive, or a pharmaceutically-acceptable salt thereof; such composition wherein the adjuvant compound is anionic and contains about eight to twenty-four, preferably eight to fourteen, carbon atoms inclusive; such composition wherein the xanthate is a compound of formula I, wherein R¹ represents benzyl, cyclohexyl, tricyclodecyl, 1-norbornyl, cyclododecyl, n-dodecyl, or 4-isobornylcyclohexyl, and wherein R² represents sodium or potassium, or $C_1-C_4$-alkyl, and, as adjuvant compound, a naturally-occurring fatty acid or a fatty alcohol sulphate with eight to fourteen carbon atoms, inclusive, or an alkali metal salt thereof; such composition wherein the xanthate is sodium or potassium-benzylxanthate, sodium or potassium-cyclohexylxanthate, sodium or potassium-1-adamantylxanthate, sodium or potassium-8(9)-tricyclo-[5-2.1.0²·⁶]-decylxanthate sodium or potassium-2-endo or exo-bicyclo[2.2.1¹·⁴]-heptyl-xanthate, sodium or potassium-cyclododecylxanthate, sodium or potassium-n-dodecylxanthate, or sodium or potassium-4-isobornyl-cyclohexylxanthate, and wherein the adjuvant compound is an aliphatic monocarboxylic acid having nine to thirteen carbon atoms, inclusive, or a sodium or potassium salt thereof, or a fatty alcohol ether sulphate, phosphate, or phosphonate with eight to eighteen carbon atoms, inclusive, or the sodium or potassium salt thereof, or an alkali metal deoxycholate; such composition wherein the adjuvant compound is the sodium or potassium salt of decanoic acid, undecanoic acid, dodecanoic acid, deoxycholic acid, dodecyl sulfate, or dodecylphosphonic acid; such composition wherein the mole ratio of the xanthate to the adjuvant compound is on the order of 1:6 to 1:0.25, preferably 1:3 to 1:0.5, and especially 1:1 to 1:2 and such composition in topical, oral, or parenteral application form, especially in the form of an ointment, a gel, or a spray, or in the form of a tablet, capsule, suppository, or an infusion or injection solution. Also, a method for the production of an antiviral and antitumor composition having enhanced antiviral and antitumor antitumor composition having enhanced antiviral and antitumor activity comprising the step of admixing into the form of a pharmaceutical composition a known antiviral and antitumor xanthate compound and an activity-enhancing amount of an ionic adjuvant compound having both a hydrophilic group and a lipophilic group; such a method wherein the mole ratio of the xanthate to the adjuvant compound is on the order of 1:6 to 1:0.25, preferably 1:3 to 1:0.5, and especially 1:1 to 1:2; and such a method wherein the adjuvant is anionic and the composition produced is in topical, oral, or parenteral application form, especially in the form of an ointment, a gel, or a spray, or in the form of a tablet, capsule, suppository, or an infusion or injection solution. Also, use of such a composition as an antiviral or antitumor agent. Moreover, a method of combating a virus or tumor which comprises administering to a subject or situs afflicted with a virus or tumor which is susceptible to treatment with a chemotherapeutic agent an amount of an antiviral and antitumor xanthate together with an activity-enhancing amount of an ionic adjuvant compound containing both a lipophilic group and a hydrophilic group, which combined amounts are effective for such antiviral or antitumor purpose; and such a method for combating a virus or tumor which comprises administering, to a subject or situs afflicted with a virus or tumor which is susceptible to treatment with such a composition, an antiviral and antitumor xanthate composition comprising an anionic adjuvant, in an amount which is effective for the alleviation of the said condition.

According to the invention, it is advantageous for the hydrophilic group, namely the carboxyl, sulphate, sulphonate, or phosphate group, of the adjuvant compound to be located at one end of the preferably elongated aliphatic portion which constitutes the lipophilic group, thus forming a polar molecule with a hydrophilic "head" and a lipophilic "body". Especially preferred carboxylic acids of this type are decanoic acid, undecanoic acid, and dodecanoic acid. The adjuvant compounds are therefore preferably compounds with an anionic hydrophilic group, which are preferably employed in the form of pharmaceutically compatible salts, especially as an alkali metal salt, and especially a sodium or potassium salt, although numerous cationic compounds such as quaternary ammonium salts are available in the prior art and may also be employed to advantage in some cases, provided they meet the other criteria set forth, e.g., lipophilic and hydrophilic moieties, as further shown hereinafter.

The carboxylic acid may also be fluorinated or perfluorinated, which means that in such carboxylic acids some or many or all of the H-atoms of the C—H-bonds may be replaced by fluorine atoms.

Further examples of adjuvant compounds of this type are fatty alcohol sulphates (sulphuric acid esters of fatty alcohols) such as, e.g., sodium dodecyl sulphate (SDS), ammonium lauryl sulphate, fatty alcohol ether sulphates (alkyl ether sulphates), e.g., R—(O—CH$_2$—CH$_2$)$_2$—OSO$_3$Na, sodium alkylsulphoacetates R—O—CO—CH$_2$—SO$_3$Na, sulphocolaurate, potassium salt of a lauric acid ester CH$_3$—(CH$_2$)$_{10}$—COO—CH$_2$CH$_2$—NH—CO—CH$_2$—SO$_3$K, alkylol amide sulphates (sulphated fatty acid alkylol amides) R—CONH—R$^1$—OSO$_3$Na (R$^1$,e.g. =CH$_2$), alkane sulphonates (and hydroxyalkane sulphonates), olefinic sulphonates, α-sulpho fatty acid esters, alkyl-(e.g., dodecyl)-benzene sulphonates, sulphosuccinates, e.g.,

| monoester | diester |
|---|---|
| SO$_3$Na | SO$_3$Na |
| \| | \| |
| HC—COOR | HC—COOR |
| \| | \| |
| H$_2$C—COONa | H$_2$C—COOR, | including dioctyl-sodium-sulphosuccinate

SO$_3$Na      C$_2$H$_5$
|           |
HC—COO—CH$_2$—CH—(CH$_2$)$_3$—CH$_3$
|
H$_2$C—COO—CH$_2$—CH—(CH$_2$)$_3$—CH$_3$,
                      |
                     C$_2$H$_5$ fatty acid condensation products, e.g., fatty acid isothionates, R—COO—CH$_2$—CH$_2$—SO$_3$Na, fatty acid methyltaurides,

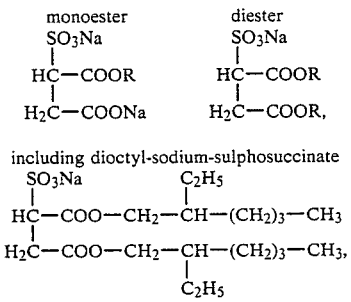

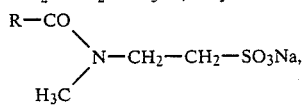

fatty acid sarcosides

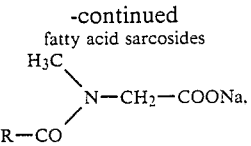

protein fatty acid condensation products (fatty acid polypeptide condensation products) such as:

$$R-CO-NH-R-(CO-NH-\overset{R}{\underset{|}{CH}})n-COOM$$

e.g., $H_{22}C_{11}-CO-NH-\overset{R}{\underset{|}{CH}}-(CO-NH-\overset{R}{\underset{|}{CH}})n-COOK,$ fatty alcohol ether phosphates (fatty alcohol phosphoric acid esters) such as:

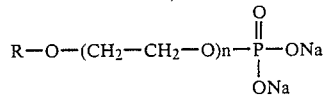

e.g., ethoxylated oleyl ether phosphate, monoglyceride sulphates such as

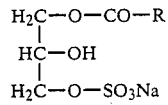

sulphoricinoleate (Turkey red oil), and Na—SO$_3$—O—C$_{17}$H$_{32}$—COONa.

The radicals R in the above-mentioned formulae are alkyl groups, the length of which is dimensioned so as to ensure that the total number of carbon atoms of each compound is in the range of about 6 to 18.

Especially advantageous are those active substances of formula I in which R$^1$ represents benzyl, cyclohexyl, 1-adamantyl, tricyclodecyl, 1-norbornyl, cyclododecyl, n-dodecyl, or 4-isobornyl-cyclohexyl, and R$^2$ represents a sodium or potassium ion, or a C$_1$-C$_4$-alkyl group.

Examples of such advantageously antiviral and antitumor active substances are the following sodium or potassium xanthates: benzyl xanthate, cyclohexyl xanthate, adamantyl xanthate (D424), 8(9)-tricyclo-[5.2.1.0$^{2.6}$]-decyl xanthate (D609), 2-endo or exo-bicyclo [2.2.1$^{1.4}$]-heptyl xanthate (D611), cyclododecyl xanthate (D435), n-dodecylxanthate, and 4-isobornyl-cyclohexyl xanthate (D622).

The active xanthate and the action-increasing adjuvant according to the invention are advantageously present in a mol ratio of 1:6 to 1:0.25, preferably a mol ratio of 1:3 to 1:0.5, particularly a mol ratio of 1:1 to 1:2 ( active xanthate: adjuvant compound). The compositions according to the invention may be applied topically, orally, or parenterally. Suitable oral or parenteral application forms are tablets, capsules, suppositories, and infusion or injection solutions. These application forms are prepared with the usual pharmaceutically-compatible adjuvants, exipients, and diluents.

The dosage to be employed depends principally on the specific application form and on the purpose or objective of the application, e.g., of the therapy or the prophylaxis. The size of the single dose as well as the application regimen may be determined most conveniently by means of an individual evaluation of the respective case. Usually the therapeutically-active amount of the combination according to the invention, employed for an injection, lies in a dose range of approximately 0.005 to approximately 10 mg per kg of body weight, preferably in the range of approximately 0.01 to approximately 0.1 mg per kg of body weight. In addition to the combination according to the invention, these oral or parenteral application forms usually contain a buffer, which maintains the pH value between approximately 7 and 8, particularly at about 7.4, and additionally sodium chloride, mannitol, or sorbitol for isotonic adjustment. They may also be prepared in lyophilized or solidified form. Of course, when the object is to kill a virus outside a living animal body, the combination may be employed without therapeutic or pharmaceutical considerations.

A suitable preparation for topical application may be prepared on an aqueous basis, e.g., by dissolving the combination according to the invention in an aqueous buffer solution and subsequently adding a polymeric thickening agent, e.g., polyvinyl pyrrolidone.

A suitable oleaginous application form for topical application may be obtained for example by suspending the combination according to the invention in an oil, subsequently adding a swelling agent such as aluminum stearate and/or a vegetable active agent or tenside, the HLB-value (hydrophilic-lipophilic-balance) of which is suitably below about ten, such as a fatty acid mono ester of a multivalent alcohol, e.g., glycerine monostearate, or sorbitan monooleate.

A suitable fatty ointment can be prepared, e.g., by suspending the two active substances according to the invention in an ointment base, and subsequently adding a tenside with an HLB-value below about ten. An emulsion ointment is obtainable in a similar manner, e.g., by mixing an aqueous solution of the two active substances according to the invention into a soft ointment base and adding a tenside with an HLB-value below about ten. All such topical application forms may also contain preservatives. The concentration of the active two substances in the total mixture is usually about 0.05 to 5 mg, preferably 0.25 to 1 mg, to approximately 100 mg of the total composition, with broader limits being up to 10 mg per 100 mg of total composition.

The xanthates of the general formula I are known and can be prepared, e.g., by the reaction of an alcoholate of the formula $R^1-O-Me$, wherein $R^1$ is as defined, and Me represents an alkali metal atom, with carbon disulphide, or by the reaction of an alcohol, which corresponds to the above-mentioned alcoholate, with carbon disulphide in the presence of a strong alkali base, in a manner known per se. Such preparation is described in the Deutsche Offenlegungsschrift (published German patent application) 31 46 772 and other published applications and patents cited hereinbefore. In this context, reference is expressly made to those published documents.

The second component of the composition according to the invention, namely the ionic adjuvant compound with both a lipophilic and a hydrophilic moiety, may illustratively be selected from commercially-available mono and dicarboxylic acids, mono and disulphate, mono and disulphonate, and mono and diphosphate compounds having a straight or branched saturated or unsaturated aliphatic group with, for example, about 6 to 18 carbon atoms. Compounds of this type may be advantageously transformed into the corresponding salts, in a manner known per se, using a base which supplies a pharmaceutically compatible salt.

Some results obtained from pharmacologic examinations are as follows:

1. Cytotoxicity

Tested substances: potassium-8(9)-tricyclo-[5.2.1.0$^{2.6}$]-decyl xanthate (D609) abbreviation: "DEXA", combined with different long-chain carboxylic acids which are identified in the following table.

Cell cultures employed: normal hamster embryo fibroblasts (HEF); hamster embryo fibroblasts transformed by bovine papilloma virus (HEF-BPV).

Medium: Eagle's basal medium with Earle's salts (BME), complemented with 10% fetal calf serum (FBS); 1% penicillin, streptomycin; pH=7.4.

Method: The indicated cell types are incubated in vitro in the indicated medium. To each sample a combination consisting of 20 μl of the above-mentioned active substance DEXA and stepwise increasing amounts of a fatty acid (indicated in the following Table) is added. After three days the cultures are examined microscopically, thus determining the minimal toxic concentration. The results are summarized in the following Table.

TABLE 1

| Tested combination | HEF-culture | HEF-BPV-culture |
|---|---|---|
| | minimal toxic concentration of 20 μg/ml DEXA + adjuvant | |
| DEXA + adjuvant | adjuvant μg/ml | adjuvant μg/ml |
| DEXA + decanoic acid | 100 | 10 |
| DEXA + undecanoic acid | 100 | 10 |
| DEXA + dodecanoic acid | 40 | 10 |
| DEXA + myristic acid | 30 | 10 |

Table 1 shows that the combination of the active substance DEXA and a fatty acid is considerably more toxic to the transformed cell culture than to the cell culture which had not been transformed. This applies particularly to the combination with decanoic acid and undecanoic acid, which combinations are ten (10) times as toxic to the transformed cell culture than to the normal cell culture.

In a further cytotoxicity test, different combinations according to the invention were tested, with respect to their toxicity, in cell cultures of mice embryo fibroblasts (MEF) and transformed mice embryo fibroblasts (MEF-K1). These cell cultures were incubated in the following medium: BME, 5% calf plasma, penicillin, streptomycin, pH=7.4. The tests were carried out analogously to the above-mentioned indications, but with the difference that the microscopic evaluation was carried out after 24 hours. The results are summarized in the following Table 2.

TABLE 2

| Tested combination | MEF | MEF-K1 |
|---|---|---|
| | minimal toxic concentration of 20 μg/ml DEXA + adjuvant | |
| DEXA + adjuvant | adjuvant μg/ml | adjuvant μg/ml |
| DEXA + K-decanoate | 80 | 10 |
| DEXA + decanoic acid | — | 40 |
| DEXA + undecanoic acid | 80 | 10 |
| DEXA + K-undecanoate | 80 | 10 |
| DEXA + dodecanoic acid | 60 | 20 |
| DEXA + tridecanoic acid | 60 | 10 |
| DEXA + tetradecanoic acid | 80 | 10–20 |

Table 2 shows that the tested combinations are far more toxic to transformed cell cultures than to normal cell cultures.

The selectivity of the toxic action of DEXA combined with undecanoic acid against transformed cell cultures is even more evident in the following test, which is based upon the introduction of tritium-labeled uridine ($^3$H-uridine).

Normal mice embryo fibroblasts (MEF) and mice embryo fibroblasts transformed with bovine papilloma virus (MEF-BPV) were sown on Linbro-plates ($2 \times 10^5$ cells per hole) and treated with a combination of 20 μg/ml DEXA and increasing amounts (10, 20, 40, 60, and 80 μg/ml) of undecanoic acid. As medium, Eagle's basal medium with Earle's salt, complemented with 5% calf plasma, pH 7.5 in an atmosphere with 5% $CO_2$, was employed. After two days new medium was added, which contained 1 μCi/ml of $^3$H-uridine, but which did not contain the active substance mentioned above. Two hours later the amount of $^3$H-uridine, which can be precipitated with acid, is determined in each culture. Before performing the total count the low-molecular weight components, including the $^3$H-uridine which has not been incorporated, are washed out. Thereafter the counts are made on the dry culture. The average values of the radioactivity measured in two (2) cultures are shown in FIG. 1.

The diagram of FIG. 1 shows that the transformed cell cultures are destroyed or inactivated selectively by the inventive combination, due to the fact that radioactivity, that is to say $^3$H-uridine, is found only in the normal cell culture, but not in the transformed cell culture.

2. Antiviral Action

The inhibitory action of the active substance DEXA, of the combination of DEXA and decanoic acid in different concentrations, and of decanoic acid alone was tested in different in vitro cultures, inoculated with herpes simplex virus 1 (HSV1-culture). The medium had a pH of 7.4. After two days of incubation the virus yield was determined and plaque-forming units (pfu), which is indicated in percent, calculated with respect to a corresponding culture without inhibitory additaments, as shown in the following Table.

TABLE 3

| Tested inhibiting compounds | % pfu, referred to a virus culture without inhibitors |
| --- | --- |
| DEXA (20 μg/ml) | 22.6 |
| DEXA (10 μg/ml) + decanoic | |
| acid 10 μg/ml | 8.7 |
| 20 μg/ml | 0 |
| 40 μg/ml | 0.3 |
| decanoic acid | |
| 10 μg/ml | 18.9 |
| 20 μg/ml | 24 |
| 40 μg/ml | 35 |

Table 3 shows that the combination of DEXA and decanoic acid develops a significantly stronger inhibitory action than the individual components of the combination.

A combination of DEXA and sodium dodecylsulphate (SDS) similarly strongly inhibited the reproduction of HSV1.

Cells: Rita P O/37
Medium: BME, 5% FBS, 1% penicillin+streptomycin, pH 7.4, 5% $CO_2$ atmosphere
Inhibitors: 10 μg/ml DEXA+10, 20, 40, 80 μg/ml dodecylsulphate (SDS)
Infection of the Rita cells with MOI: 0.05 pfu/cell
Addition of inhibitors: One hour after infection (2 cultures each)

Re-collection of the virus descendants: 24 hours after infection
Control titer: $7.7 \times 10^6$ pfu/ml

| combination of active substances | titer pfu/ml | inhibiting factor |
| --- | --- | --- |
| 10 μg/ml DEXA + 10 μg/ml SDS | $2.5 \times 10^2$ | $3 \times 10^4$ |
| 10 μg/ml DEXA + 20 μg/ml SDS | 25 | $3 \times 10^5$ |
| 10 μg/ml DEXA + 40 μg/ml SDS | 25 | $3 \times 10^5$ |
| 10 μg/ml DEXA + 80 μg/ml SDS | 2.5 | $3 \times 10^6$ |

The growth of uninfected Rita cells was practically uninhibited by the same combination of active substances.

Analogous results were obtained with a combination of cyclododecyl xanthate (D435) and undecanoic acid. This combination was also tested, e.g., on confluent cells of human embryolungs infested with HSV-1, with very efficient inhibitory results. The same effect is obtained when using D424, D611, or D622 in place of D609.

It has also been found that RNA-virus (single cord virus) such as, e.g., vesicular stomatitis virus, is inhibited by the combination of active substances as described in the foregoing.

In a further test carried out on guinea-pigs with HSV-infested lesions, the healing effect of the combination according to the invention and of the adjuvant alone was tested. The substances identified in Table 4 were admixed in a vaseline ointment at the concentrations mentioned, and the ointment was then applied to the HSV-induced lesions on the skin of the guinea-pigs (twice daily).

The results are shown in the following Table 4.

TABLE 4

| | number of lesions | | |
| --- | --- | --- | --- |
| treating agent | at the beginning of treatment (96h after inoculation) | after 36 h of treatment | % cure |
| vaseline with 10% decanoic acid | 8 | 8 | |
| | 10 | 10 | 0 |
| | 9 | 9 | |
| vaseline with 5% DEXA + 10% decanoic acid | 6 | 4 | |
| | 23 | 14 | |
| | 16 | 5 | 42 |
| | 11 | 8 | |
| | 8 | 6 | |

Table 4 shows that by far the best healing results were obtained with a combination according to the invention.

In a further test for the antiviral action of the combination, six (6) guinea-pigs were inoculated with HSV-1 of the Wal lineage. Eighteen (18) hours later the treatment (twice daily), with a vaseline ointment containing 5% DEXA and 5% decanoic acid, was begun. After two days of treatment (72 hours after inoculation) the animals were killed and the infested skin was removed. The skin was frozen with liquid nitrogen and then comminuted in a beater mill "Mikro Dismembrator" (tm) (two samples per animal), re-collecting it afterwards in a tenfold amount (w/v) tissue culture medium. After a short centrifugation (one minute, Eppendorf-desk top centrifuge) the virus titer of the overhead layer was determined.

Result: No virus detectable. The titer of a blank test medium was $1 \times 10^5$ pfu/gram of tissue.

Figure 3:
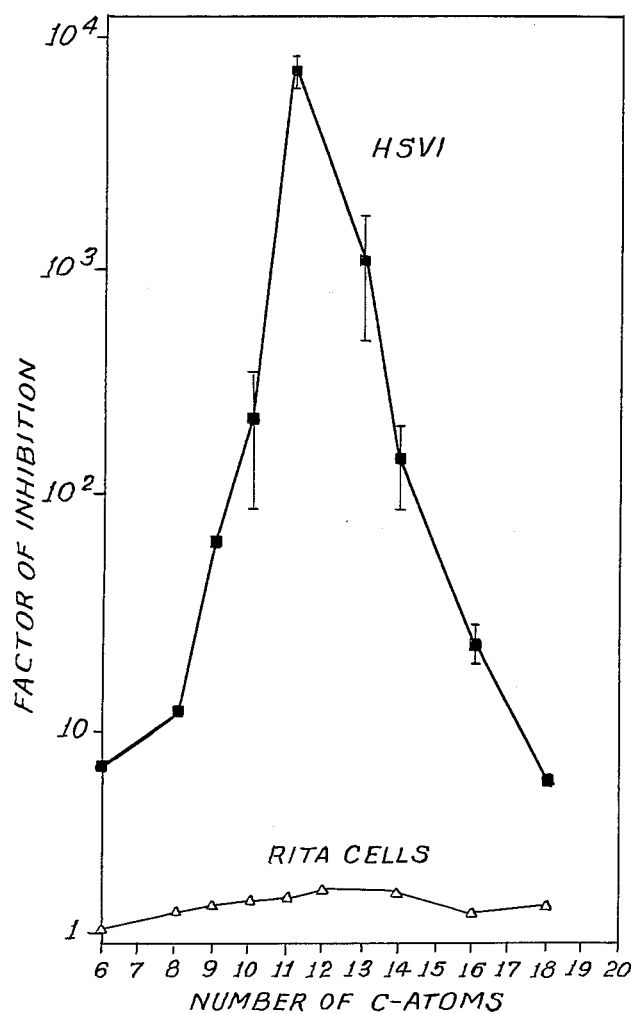
FIG. 3 is a graph depicting the influence of the chain length of monocarboxylic acids on the antiviral activity and cytotoxicity in combination with D609 on both uninfected and HSV-1-infected Rita cells.

The influence of the chain length of monocarboxylic acids on the antiviral activity and cytotoxicity in combination with D609 is shown in FIG. 3. Uninfected ∆ and HSV-1-infected ■ Rita cells were treated with 10 µg/ml D609 and 40 µg/ml of each monocarboxylic acid (at pH 7.4).

The virus yield of two cultures was examined individually by plaque assay in duplicate. Error bars indicate standard deviation. Cell densities of duplicate uninfected treated and untreated Rita cell cultures were determined after staining with trypan blue by counting with a hematocytometer.

3. Antitumor Activity

Treatment of lymphatic leukemia in mice.

Six week old DBA-2 mice were intravenously inoculated with $1 \times 10^5$ tumor cells (NCI-Egg-Leukemia). Eighteen (18) hours later three groups of ten (10) animals each were formed. One group did not receive any treatment and represented the control group. The second group was treated only with DEXA ($4 \times 15$ mg/kg, then $6 \times 11$ mg/kg). The third group was treated with a combination according to the invention, namely DEXA and undecanoic acid (DEXA treatment as performed in group 2, additionally undecanoic acid $4 \times 7.5$ mg/kg, then $6 \times 5.5$ mg/kg).

All applications were made intravenously. The injections were given in periods of one hour. The following day (2 days after inoculation with tumor cells) blood samples were taken from each animal, and the lymphocyte concentration was determined. The results are summarized in the following Table 5.

TABLE 5

| number of lymphocytes $\times 10^{-6}$/ml | | |
|---|---|---|
| untreated | DEXA | DEXA + undecanoic acid |
| 13.8 | 17.9 | 8.6 |
| 11.1 | 15.0 | 11.7 |
| 15.8 | 24.1 | 12.0 |
| 17.3 | 13.0 | 9.8 |
| 12 | 18.6 | 12.8 |
| 15.7 | 15.6 | 18.4 |
| 23 | 10.7 | 11.6 |
| 18.3 | 14.6 | 12.4 |
| 20.2 | 13.7 | 8.4 |
| | | 10.8 |
| average value $\times 10^{-6}$/ml | | |
| 16.3 | 15.9 | 11.7 significant $p < 0.01$ |

Table 5 shows that the combination according to the invention provides a significant reduction in the number of lymphocytes.

Regression of autochthonous skin tumors in mice, upon systemic treatment with a combination according to the invention, comprising DEXA and undecanoic acid.

Skin tumors were induced in a way known per se in seven week old female mice of the NMRI lineage. This involved topical treatment with a single does of 25.6 mg DMBA dissolved in 0.1 ml acetone, and seven days later with 6.16 mg TPA dissolved in 0.1 ml acetone, the latter medium being applied twice a week during 23 weeks.

Three weeks after termination of the promoter treatment, chemotherapy was started by intravenous injection of 10 mg/kg of test compound (1 mg/ml), previously dissolved in 0.9% NaCl solution with pH 7.4. The pH was adjusted by the addition of 0.15M NaOH. Forty (40) animals with tumors were selected, forming four (4) arbitrary groups. Eleven (11) animals were not treated, ten (10) animals were treated with DEXA, ten (10) animals were treated with undecanoic acid, and nine (9) animals were treated with a combination of DEXA and undecanoic acid (1 mg per ml, 10 mg/kg of each substance).

Figure 2:
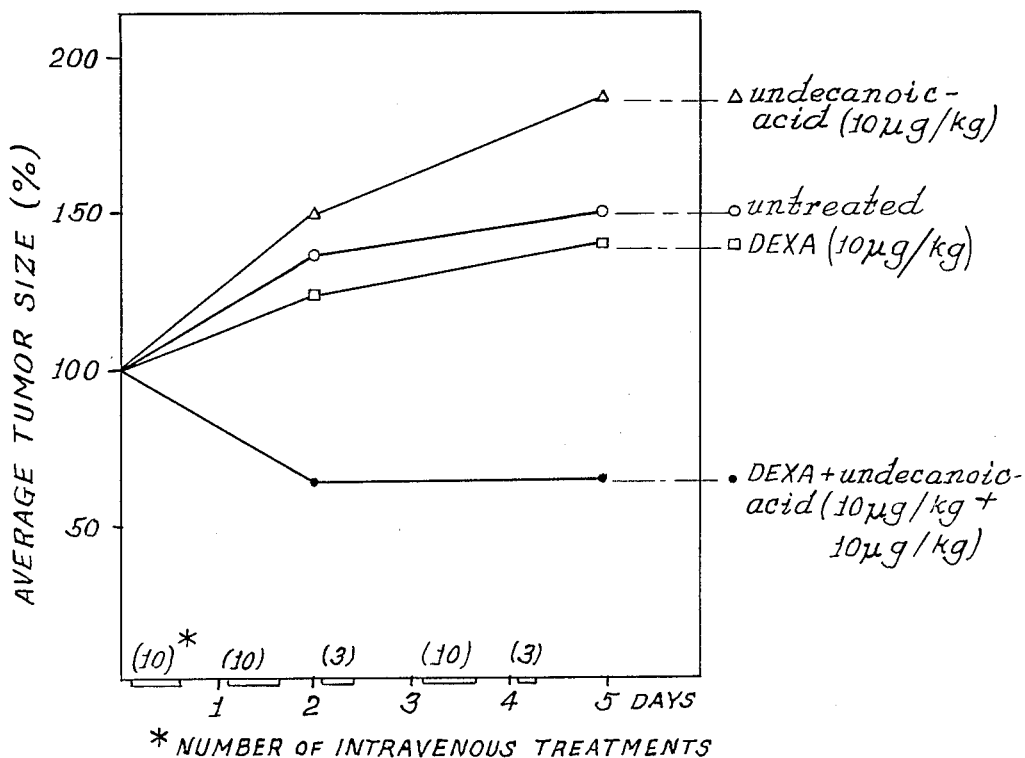
FIG. 2 is a graph depicting response of induced skin tumors to intravenous (IV) treatment with compositions of the invention and individual components thereof at correlatable concentrations (10 mg/kg).

In the illustrative FIG. 2 the times of injection are indicated by means of small rectangles on the time axis. The size of all tumors (3 dimensions) was determined with a sliding caliper. Thus, the size of 35 tumors of untreated animals, 40 tumors of animals treated with undecanoic acid, 37 tumors of animals treated with DEXA, and 35 tumors of animals treated with the combination according to the invention, was determined. The initial size of the tumors varied between 2 and 400 mm$^3$. The size of each single tumor was observed during the test. Accretion or regression was expressed in percent of the initial size. The average values of each group are indicated in FIG. 2. The significance of the regression in tumors treated with the combination according to the invention was calculated according to the Student's T-Test. After two (2) days of treatment, the size of the tumors in the treated group differed considerably from those in the untreated group, being of $p < 10^{-10}$, and after five days of treatment at $p < 10^{-7}$.

Subcutaneous Treatment of Autochthonous Skin Tumors.

Twenty (20) test animals (of the type described) with chemically-induced skin tumors, produced as described, were divided arbitrarily into four (4) groups. The treatment was carried out by subcutaneous injection in the immediate vicinity of the tumors, injecting three portions of 0.5 ml every two hours during two days. On the third day a single dose was injected. The injection solution contained 5 mg/ml DEXA and 5 mg/ml undecanoic acid. Six days after starting the treatment, a photographic and visual evaluation was made.

Result: All tumors had regressed considerably, many had disappeared completely, and all had reduced their initial size by at least 50%.

Regression of autochthonous skin tumors in mice upon systemic treatment with a combination according to the invention, comprising DEXA and undecanoic acid.

Skin tumors were produced on NMRI-mice as previously described. Two days after the last TPA-application, the chemotherapy was started. The treatment agent was administered to the animals by intravenous injection three times a day. Each injection contained 10 mg/kg DEXA and 10 mg/kg undecanoic acid (1 mg/ml of each compound, dissolved in 0.9% NaCl). The pH of the solution was adjusted to pH 7.4 with 0.15M NaOH. The animals were photographed at the beginning and at the end of the treatment, determining the number of tumors of each animal. Four (4) weeks after termination of the therapy, the tumors were evaluated again. No recidives (recurrences) were visible on the sites where the tumors had disappeared. The results are summarized in the following Table 6.

TABLE 6

| test animal | number of tumors | | treatment agent |
|---|---|---|---|
| | before treatment | after treatment | |
| 1 | 3 | 3 | |
| 3 | 5 | 3 | |

TABLE 6-continued

| test animal | number of tumors before treatment | number of tumors after treatment | treatment agent |
|---|---|---|---|
| 4 | 14 | 4 | |
| 5 | 11 | 8 | |
| 6 | 5 | 3 | |
| 7 | 5 | 0 | DEXA + |
| 8 | 15 | 10 | undecanoic |
| 9 | 13 | 0 | acid |
| 10 | 14 | 4 | i.v. |
| 11 | 6 | 2 | |
| total | 91 | 37 | = 59% regression |
| 1 | 11 | 10 | |
| 2 | 4 | 3 | |
| 3 | 8 | 7 | |
| 4 | 4 | 2 | |
| 6 | 4 | 0 | Control |
| 7 | 7 | 7 | |
| 8 | 5 | 5 | |
| 9 | 10 | 8 | |
| 10 | 4 | 1 | |
| 11 | 7 | 5 | |
| total | 64 | 48 | = 25% regression |

Table 6 shows that a combination according to the invention, which contains DEXA and undecanoic acid, produces a regression of skin tumors at a rate of 59%, whereas the regression in untreated animals was only 25%.

Further test data regarding the antiviral and antitumor compositions of the invention follows:

(A) Antiviral Activity of D609/Undecanoic Acid

Xanthate compounds have been shown to exhibit antiviral activity against various DNA and RNA viruses under acidic pH conditions (Sauer, G., Amtmann, E., Melber, K., Knapp, A., Müller, K., Hummel, K., and Scherm, A.: DNA and RNA virus species are inhibited by xanthates, a class of antiviral compounds with unique properties. Proc. Natl. Acad. Sci. USA 81, 3263–3267 (1984)). It is now possible more effectively to utilize the unique broad range antiviral spectrum of these compounds under higher and physiological pH conditions (pH 7.4) by simultaneous or combination administration of certain ionic adjuvants having both a hydrophilic and a lipophilic moiety. Thus, tricyclodecan-9-yl-xanthate (D609), in combination with the adjuvants sodium deoxycholate, sodium dodecylsulfate, and certain fatty acids, which have no antiviral activity of their own, inhibits the replication of various DNA and RNA viruses (such as herpes simplex, vesicular stomatitis and Coxsackie B 4) in vitro at pH 7.4 (Table 7). Among saturated fatty acids of various chain lengths there was a marked size advantage in that the efficiency of undecanoic acid (11 C atoms) was three orders of magnitude greater than that of shorter (8 C atoms) or longer (18 C atoms) monocarboxylic acids. Dose-response kinetics revealed that a dose which inhibited the replication of herpes virus by a factor of 1000 still permitted mitotic activity in uninfected growing control cultures. A mixture in a 1:1 ratio D609/undecanoic acid turned out to be most advantageous as may be seen from FIG. 4 (solid circles).

Figure 5:
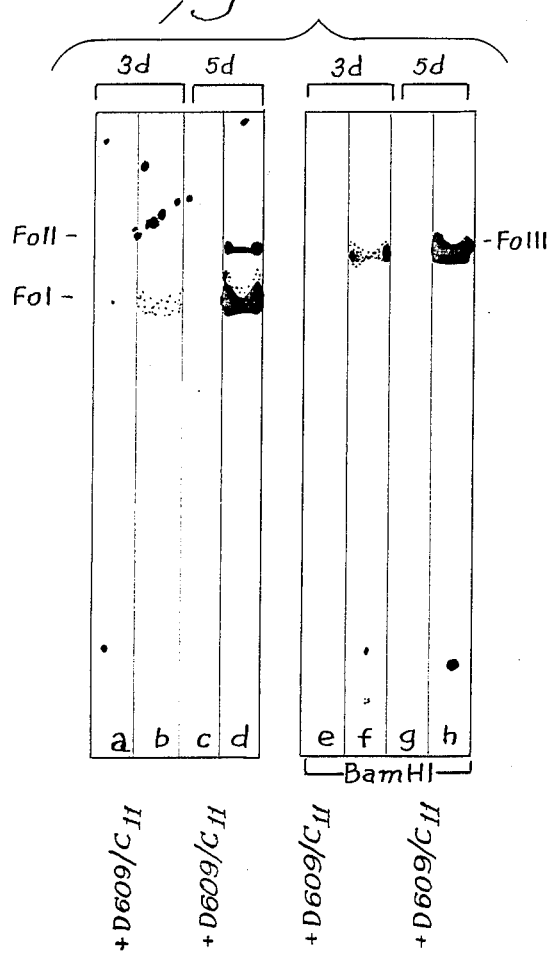
FIG. 5 depicts a gel electrophoresis pattern evidencing complete inhibition of replication of HTLVIII virus.

Similar data were obtained also in the case of HTLVIII virus which could be inhibited in tissue culture by 10 μg of D609 combined with 10 μg of undecanoic acid/ml after application periods of three and five days (FIG. 5). The treatment with the combination leaves the mitotic activity of mitogen-stimulated perih- eral human blood lymphocytes unaffected at such concentrations which are capable of killing B- and T-cell lymphomas (See Section B, which begins later on in this Specification, relating to the antitumor effect or activity of the compounds of this invention, especially FIGS. 6 and 8 and the discussion concerning these Figures.). This renders the D609/undecanoic acid combination potentially suitable for the chemotherapy of AIDS.

TABLE 7

Antiviral effect of the combination D609/undecanoic acid on RNA viruses at pH 7.4

| Virus species | D609 [μg/ml] | Undecanoic acid [μg/ml] | Virus yield[a] [pfu/ml] |
|---|---|---|---|
| VSV[b] | 0 | 0 | (4.3 ± 1) × 10$^6$ |
| | 5 | 0 | (5.6 ± 0.05) × 10$^6$ |
| | 0 | 40 | (4.3 ± 0.3) × 10$^6$ |
| | 5 | 40 | (1.3 ± 0.2) × 10$^4$ |
| Coxsackie B4 | 0 | 0 | (1.15 ± 0.2) × 10$^6$ |
| | 10 | 40 | (7.7 ± 0.25) × 10$^4$ |

[a,b] Values were obtained by assaying duplicate cultures, and the resulting virus yields were determined in duplicate. VSV progeny was harvested 10 h, and Coxsackie B4 at 24 h, after infection.

Figure 4:
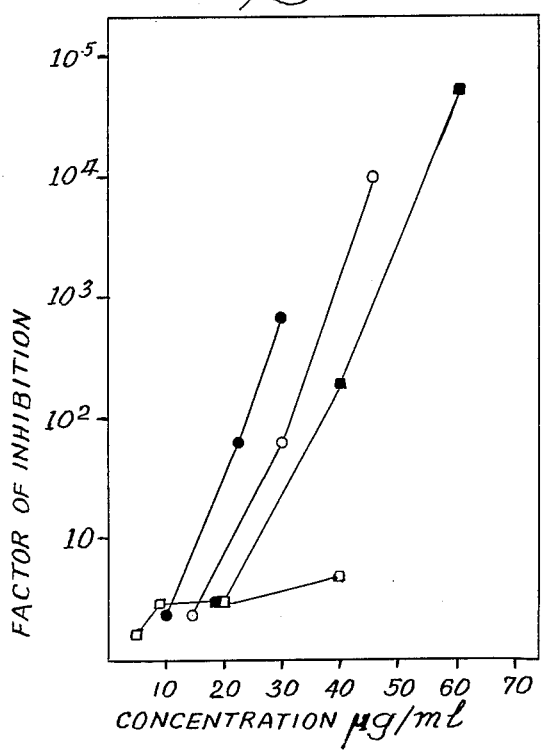
FIG. 4 is a graph depicting the inhibition of herpes virus growth by various concentrations of D609 in combination with undecanoic acid in various ratios.

FIG. 4: Inhibition of herpesvirus growth by various concentrations of D609 and undecanoic acid.

The concentration of both components is indicated in the abscissa. D609 and undecanoic acid were mixed in the following ratios:

● 1 : 1; 01:2; ■ 1: 3; □ 0 1 (undecanoic acid).

Concentrations resulting in an inhibition of more than a factor of 10$^3$ were accompanied by cytotoxic effects. Lower concentrations, however, did not cause recognizable cytotoxicity in uninfected control cells.

A concentration of 1:1 (D609/undecanoic acid, ●) was found to be most efficient with regard to the concentration of either compound and their combined antiviral effect. Hence, it is suggested to apply the compounds in a 1:1 ratio.

FIG. 5: HTLVIII specific nucleic acid (superhelical DNA as a replicative intermediate) was isolated and visualized after gel electrophoresis and hybridization with cloned authentic radioactively-labeled HTLVIII DNA. After treatment for 3 days (lane a) and 5 days (lane c) the signal that is typical for HTLVIII DNA is completely abolished whereas, in untreated infected (K37 T-lymphoma) cultures (lanes b and d), the HTLVIII specific DNA can be seen (both the superhelical form I and the relaxed circular form II DNA). After cleavage with a single-cut restriction endonuclease, form I and II are converted to the linear form III (lanes f and h). These data show that, after such treatment, the replication of HTLVIII can be completely inhibited.

(B) Antitumor Activity of D609/Undecanoic Acid

Xanthate compounds with antiviral properties exert in combination with monocarboxylic acids of a discrete size (preferably 11 or 12 C-atom chain length) a pronounced antitumoral activity in vitro.

Tricyclodecan-9-yl-xanthogenate (D609) or cyclododecylxanthogenate (D435), when administered together with either undecanoic or dodecanoic acid to various transformed cells (generally displaying low serum requirement), can cause cell death. When applied at the same concentration to normal cells from which the transformed derivatives originate, such effect was either not apparent or much less severe.

This is documented by the data in Table 8 where the effect of D609/undecanoic acid on normal cells and transformed derivatives thereof is compared. The selective killing of tumor cells (and of chemically-or virally-transformed cells) is evident from the differences in the survival-rate ranging up to a factor of $10^{-6}$, which is the limit of detectability in the experimental assay systems. While normal cells remain almost unaffected by the treatment, their transformed derivatives (displaying low serum requirement) do not survive the same treatment.

Figure 6:
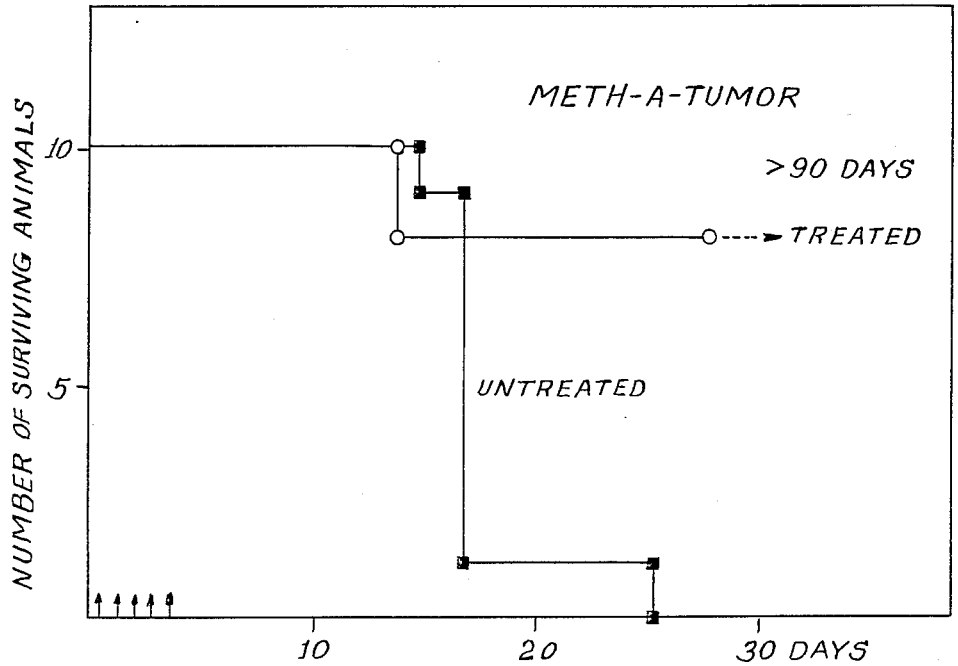
FIG. 6 is a chart showing the results of the treatment of Meth-A tumor immediately after transplantation using a combination of D609 and undecanoic acid.
Figure 7:
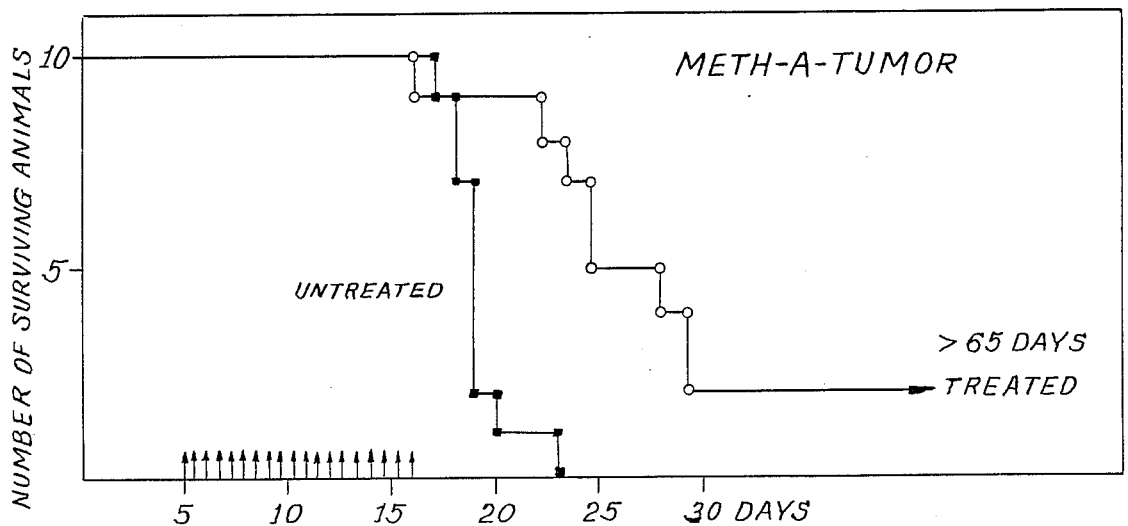
FIG. 7 is a chart showing the results of the treatment of Meth-A tumor considerably after transplantation using a combination of D609 and undecanoic acid.

The Meth-A-tumor (a fibrosarcoma) can be successfully prevented by intraperitoneal application of the D609/undecanoic acid combination (FIG. 6). Even at progressed stages (five days after inoculation) a therapeutic effect can be demonstrated (FIG. 7). Treatment in either case with D609 in the absence of undecanoic acid had essentially no demonstrable antitumor effect.

Figure 8:
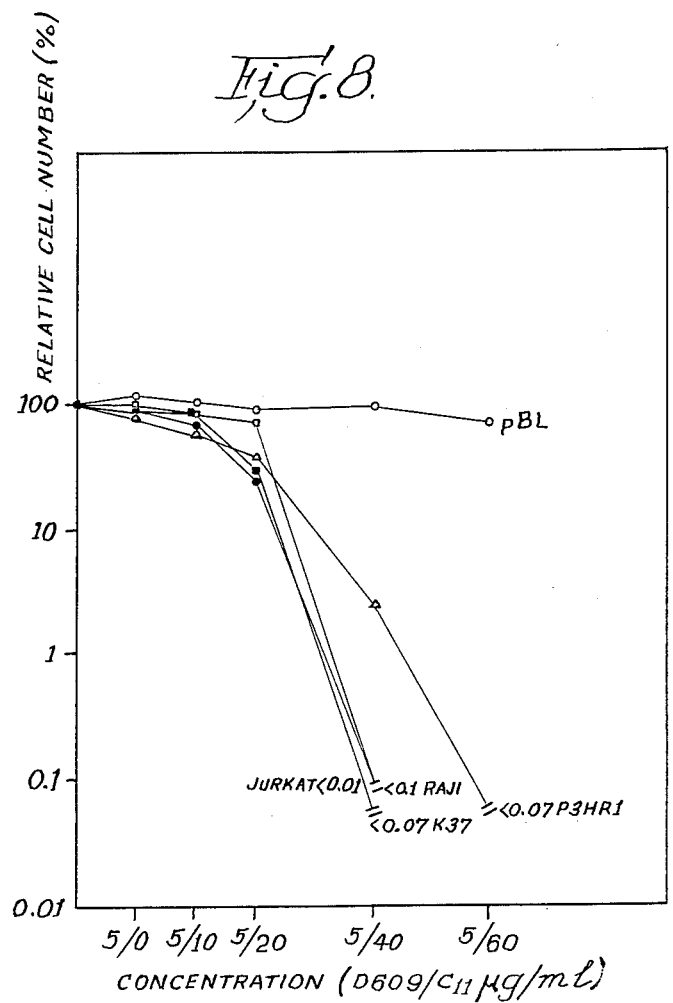
FIG. 8 is a graph showing the sensitivity of normal blood lymphocytes and T-cell and B-cell lymphomas to a combination of D609 and undecanoic acid.

Furthermore, the selective killing of various B-and T-cell lymphomas (as compared to peripheral human blood lymphocytes (pBL), which resist the treatment) is documented in FIG. 8.

tween cell number in untreated cultures and treated cultures.

§§ After 10 days of incubation at 37° C. the flasks were fixed for two minutes in 2% formaldehyde and stained for 1 minute with 0.5% crystal violet. The number of cells which had been seeded in the dishes prior to treatment indicates the maximum survival rate. In no case was it possible to detect surviving cells.

* In 6 cm petri dishes $4 \times 10^5$ cells were seeded and incubated with BME, 5% FBS, in a 5% $CO_2$ atmosphere. After 1 and 2 days the cell number was determined in two dishes for each cell line. The doubling time was extrapolated from the established growth curves.

** From each cell type $10^3$ cells were seeded in 6 cm petri dishes and incubated for two weeks in medium containing 1%, 2%, 5% or 10% FBS. Colonies were visualized by crystal violet staining after fixation in 1% formaldehyde.

FIG. 6: Treatment of Meth-A-tumor immediately after transplantation. Male Balb-c mice (8–10 weeks old, 20 gr) were inoculated with $1 \times 10^6$ tumor cells i.p. One hour after the transplantation of tumor cells treatment of the animals was initiated. Ten animals were treated

TABLE 8

| designation | cell type | species | doubling time (days)* | colony formation at low serum concentration** | survival rate |
|---|---|---|---|---|---|
| RITA | kidney | monkey | 1.9 | — | 0.73§ |
| CV-1 | " | " | 1.21 | — | 1.20§ |
| C-6 | SV40 transformed | " | 1.65 | + | $<4 \times 10^{-6}$§§ |
| MEF | embryo fibroblast | mouse | 1.14 | — | 0.60§ |
| SV3T3 | SV40 transformed | " | 0.53 | + | $<2 \times 10^{-6}$§§ |
| MEF-K1 | BPV-1 transformed | " | 0.58 | + | $<3 \times 10^{-6}$§§ |
| MCA-3F | keratinocyte | " | 1.5 | — | 0.25§ |
| MCA-3D | " | " | 1.45 | — | 0.81§ |
| HEL-30 | chemically transformed keratinocyte | " | 0.78 | + | $<2 \times 10^{-5}$§§ |
| A-PDV | chemically transformed keratinocyte | " | 0.65 | + | $<3 \times 10^{-6}$§§ |
| HEF | fibroblast | hamster | 1.73 | — | 0.67§ |
| HEF-BPV | BPV-1 transformed | " | 0.48 | + | $<2 \times 10^{-6}$§§ |
| Hela | cervix carcinoma | man | 1.0 | + | $<3 \times 10^{-6}$§§ |
| HEL | fibroblast | " | 2.35 | — | 0.54§ |
| HTB72 | malignant melanoma | " | 2.9 | + | 0.087§ |
| MRC-5 | fibroblast | " | 2.9 | — | 0.80§ |
| SV-80 | SV-40 transformed fibroblast | " | | + | $<4 \times 10^{-6}$§§ |
| Wi-38 | fibroblast | " | 2.85 | — | 0.73§ |

TABLE 8

Sensitivity to Xanthate/Monocarboxylic Acid Treatment and Growth Characteristics of Various Cell Types Cells were seeded at a density of $3.8 \times 10^4/cm^2$ in plastic flasks or petri dishes. New tissue culture medium (basal medium Eagle supplemented with 2.2 g NaHCO$_3$, 1% penicillin and streptomycin (BME) and 5% fetal bovine serum (FBS)) with 10 μg/ml D609 and 40 μg/ml undecanoic acid or without the combination was added 4 h after seeding of the cells and the cultures were incubated in a 5% $CO_2$ atmosphere ($\doteq$ pH 7.4±0.05) at 37° C. (controls and treated cultures in duplicate each). After 24 h the tissue culture medium was replenished, using BME supplemented with 10% FBS.

Cells were trypsinized 24 h after removal of D609/undecanoic acid and the number of viable cells was determined in a Neubauer hematocytometer after trypan blue staining. The survival rate is the ratio beonce daily over a period of 5 days with 50 mg/kg D609 and 50 mg/kg K-undecanoic acid and 25 U-Insulin/kg in isotonic glucose. The substances were inoculated i.p. with 1 ml/20 g animal. Ten animals were treated with insulin in isotonic glucose alone. Eight animals of the D609/undecanoic acid treated group survived for more than 90 days.

FIG. 7: Treatment of Meth-A-tumor late after transplantation by D609/undecanoic acid. Female Balb-c mice (10–12 weeks old, 20 grams) were inoculated i.p. with $1 \times 10^6$ Meth-A tumor cells. Five days after transplantation 10 animals were treated with 50 mg/kg D609 and 50 mg/kg K-undecanoic acid+25 U Insulin/kg in isotonic glucose twice daily. The substances were dissolved in 1 ml/20 g animal. The treatment was terminated after 25 inoculations. Ten animals remained untreated as controls. Two animals of the treated group (open circles) survived for more than 65 days.

The insulin was added in the above tests to provide a necessary growth factor in the animal body for increasing glucose production and enhancement of cell growth, production, and stability.

FIG. 8: Sensitivity of normal blood lymphocytes and T-cell and B-cell lymphomas to a combination of D609 and undecanoic acid. Peripheral blood lymphocytes (pBL) were isolated by centrifugation on lymphoprep gradients. The cells were incubated in RPMI 1640 medium supplemented with 10% bovine fetal calf serum and 5 µg/ml PHA.* After 1 day the cells were collected by centrifugation and transferred into microtiter plates ($2 \times 10^5$ cells per hole) and new medium lacking PHA but supplemented with 10% IL-2** was added. D609 and increasing concentrations of undecanoic acid were added as indicated in the figure. In parallel 2 T-cell lymphomas (Jurkat and K37) and 2 B-cell lymphomas (Raji and P3HR1) were treated in the same manner. After 4 days of incubation the number of living cells was determined in each hole using the dye exclusion method (trypan blue). In the cultures of Jurkat, Raji and K37 cells, that had been treated with 5 µg D609 and 40 µg/ml undecanoic acid, no living cells could be detected. Treated human peripheral blood lymphocytes (pBL), however, were still able to undergo mitotic divisions despite the same treatment.

* PHA is phythoemogylutinine
** IL-2 is Interleukine-2 treated and treated cultures is indicated (mean value from two cultures) in the table.

RESULT: The cationic adjuvant (TNCB) exhibits much reduced specific antiviral adjuvant activity when compared with undecanoic acid ($C_{11}$).

Although the active antiviral and antitumor xanthates of the invention, especially D609, when used alone appear to exert their antiviral activity more effectively at an acid pH of 6.8 than at slightly higher pH's of 7.25–7.8, their combinations with an ionic adjuvant according to the invention are effective inhibitors of viral growth at a physiological pH of about 7.4. Thus, in further investigations, Rita cell cultures were treated for one day after infection with HSV-1 with D609 and at the same time with one of the adjuvants listed in Table 9. (A D609-to-adjuvant ratio of 1:4 was selected on the basis of preliminary experiments). The yield of viral progeny was determined by plaque assays and compared with the yield from untreated infected cultures. Combined treatment with D609 and any one of the first three adjuvants listed in Table 9 led to a striking inhibition of HSV-1 growth at pH 7.4. The enhanced antiviral effect cannot be attributed to increased cytotoxicity, since between 62.5% and 83% of the uninfected control cells subjected to the same treatment as infected cultures were still able to undergo mitotic division (Table 9). The last three adjuvants in the Table displayed minimal antiviral effect when compared with the first three in the Table.

TABLE 9

Antiviral activity of D609 in combination with different adjuvants at pH 7.4

| Designation of compound | Structure | Antiviral activity[a] | Cytotoxicity[b] |
|---|---|---|---|
| Undecanoic acid | $CH_3(CH_2)_9COOH$ | $5.8 \times 10^3$ | 1.6 |
| Sodium deoxycholate | $C_{23}H_{39}O_2COONa$ | $1.0 \times 10^3$ | 1.2 |
| Sodium dodecylsulfate | $CH_3(CH_2)_{11}OSO_3Na$ | $7.2 \times 10^3$ | 1.6. |
| Dodecylphosphate | $CH_3(CH_2)_{11}OPO_3H_2$ | 10.4 | n.d. |
| Dodecylphosphonic acid | $CH_3(CH_2)_{11}PO_3H_2$ | 2.8 | 1.4 |
| Dodecyltrimethylammoniumbromide (TNCB) | $CH_3(CH_2)_{11}N(CH_3)_3 + Br-$ | 15 | 1.6 |

[a]Infected (HSV-1) RITA cell cultures in duplicate were treated separately for 23 h after the period of adsorption (1 h) with 10 µg/D609 and 40 µg/ml of each detergent. The viral progeny was titrated in duplicate plaque assays and compared with the yield from untreated cultures. The antiviral activity is expressed as the factor of inhibition of virus production.
[b]Uninfected RITA cells were treated in duplicate as described above, and the cell number was determined by counting in a Neubauer counting chamber. The ratio of untreated to treated cultures is indicated (mean values from two cultures in each case).

Comparison of the antiviral activity of the combinations of D609/undecanoic acid and D609/dodecyltrimethylammoniumbromide at pH 7.4

| compound | antiviral activity[a] | cytotoxicity[b] |
|---|---|---|
| undecanoic acid ($C_{11}$) | $5.8 \times 10^3$ | 1.6 |
| dodecyltrimethylammoniumbromide (TNCB) | 15 | 1.6 |

(a) HSV-1 infected Rita cells (MOI=0.01 pfu/cell) in duplicate were treated for 23 h after the period of adsorption with 10 µg/ml D609 and either 40 µg/ml $C_{11}$ or 20 µg/ml TNCB in BME, 5% FBS, 1% penicillin and streptomycin, pH 7.4. The viral progeny was determined in plaque assays and compared with the yield from untreated cultures. The antiviral activity is indicated as the factor of inhibition of the viral titer (mean values from two cultures).

(b) Uninfected Rita cells were treated as described in (a) and the cell number was determined by counting in a Neubauer counting chamber. The ratio between un- Further Evidence of Inhibition of the HTLVIII-Virus by combination of DEXA/Undecanoic Acid K37-cells (human T-cell lymphoma) were used for the reproduction of the HTLVIII-virus. The K37-cells infected with HTLVIII were treated for a period of three or five days after the infection with 10 µg DEXA and 10 µg undecanoic acid/ml. The K37-cells still grow under these conditions as was evident from cell counts (after vital staining) before the beginning and at the end (five days) of the treatment. Furthermore, the same amount of cellular mRNA (Northern Blot) was found in the treated as well as in the untreated cells. At the same time the DNA has been isolated from said treated as well as from said untreated infected K37-cultures, and hybridized with cloned authentic HTLVIII-DNA, which has been labelled with $^{32}p$, and the result has been presented autoradiographically. A replication intermediate of the HTLVIII-virus is the superhelical DNA as is the case for all retroviruses. Said superhelical DNA (form I) and also the relaxed form II can be seen in the untreated infected cultures after three as well as after five days in the form of black dots in the autoradiogram (FIG. 5b and d). d). After cutting with a single cut restriction enzyme, which opens the annular DNA to give a linear DNA of unity length, the typical signals (FIG. 5f and h) are obtained again after three and five days, respectively. It was not possible to detect in the treated culture after three or after five days either superhelical DNA(FIG. 5a and c) or after cutting linear DNA(FIG. 5e,f). Said results show that the treatment with DEXA/undecanoic acid inhibits the replication of HTLVIII completely.

Said inhibition takes place in the K37-cells at a concentration which does not toxically damage uninfected k37-cells. Only an increase of the concentration leads to a selective destruction, not only of the K37-T-lymphoma cells but also of other human T- and B-lymphoma lines, as can be seen from FIG. 8. The combination of DEXA/undecanoic acid, however, leaves mitogen-stimulated human peripheral lymphocytes (pBL) undamaged at concentrations which are selectively lethal for tumor cells.

For this purpose, peripheral blood lymphocytes were isolated by centrifugation over lymphoprep-gradients. The cells were incubated in RPMI 1640 medium, to which 10% fetal bovine serum and 5 μg/ml phythaemagglutinine (PHA) has been added. After one day the cells were pelleted by centrifugation and transferred to microtiterplates ($2 \times 10^5$ cells per cavity) in new medium without PHA, which increasing contained, however, 10% interleukine-2. DEXA and increasing concentrations of undecanoic acid were added as is shown in FIG. 8. Parallel to this, T-cell lymphomas (Jurkat and K37) as well as B-cell lymphomas (Raji and P3HR1) were treated in the same manner. After an incubation of four days, the number of living cells was determined by color-exclusion processes (trypan blue). In the Jurkat-, Raji-, and K37-cultures, which were treated with 5 μg DEXA and 40 μg/ml undecanoic acid, no living cells were found. Treated human peripheral blood lymphocytes were, however, able to perform mitotic division even under these conditions.

In conclusion, from the foregoing, it is apparent that the present invention provides a novel antiviral and antitumor composition comprising a known antiviral and antitumor xanthate plus an activity-enhancing adjuvant which is an ionic compound having both lipophilic and hydrophilic moieties, a process for the preparation thereof, and a method of using the same to combat viruses and tumors, all having the foregoing enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. In an antiviral and antitumor composition comprising (a) a known antiviral and antitumor xanthate the improvement comprising inclusion of (b) a potintieting amount of an ionic adjuvant compound containing both a lipophilic group and a hydrophilic group.

2. Composition of claim 1 wherein the xanthate (a) has the formula I:

wherein $R^1$ represents norbornyl, tricyclodecyl, benzyl, $C_3$–$C_{20}$-alkyl, $C_3$–$C_{20}$-cycloalkyl, furyl, pyridyl, quinuclinidyl; $C_3$–$C_{20}$-alkyl substituted by hydroxy, $C_1$–$C_4$-alkoxy, or halogen; or $C_3$–$C_{20}$-cycloalkyl substituted by hydroxy, $C_1$–$C_4$-alkoxy, $C_1$–$C_4$-alkyl, or halogen; and $R^2$ represents a monovalent or multivalent metal atom, $C_1$–$C_6$-alkyl, $C_1$–$C_6$-alkyl substituted by hydroxy, $C_1$–$C_4$-alkoxy, amino, $C_1$–$C_4$-alkylamino, $(C_1$–$C_4$-alkyl$)_2$-amino, $(C_1$–$C_4$-alkyl$)_3$-ammonium, or halogen; or 2,3-dihydroxypropyl or ω-hydroxy-$(C_1$–$C_4$-alkoxy)-methyl.

3. Composition of claim 2, wherein the adjuvant compound is one in which the lipophilic group comprises an aliphatic group with six to eighteen carbon atoms, inclusive, and the hydrophilic group comprises one or two carboxyl, sulphate, sulphonate, or phosphate groups, or a pharmaceutically-acceptable salt thereof.

4. Composition of claim 2, wherein the adjuvant compound is an aliphatic mono or dicarboxylic acid, or such an acid which is fluorinated, or an aliphatic mono or disulphate, mono or disulphonate, or mono or diphosphate, in any event having six to eighteen carbon atoms, inclusive, or such a compound having one or two ether or amide groups, or a pharmaceutically-acceptable salt thereof.

5. Composition of claim 2, wherein the adjuvant compound is an aliphatic monocarboxylic acid with nine to twelve carbon atoms, inclusive, or such an acid which is fluorinated, or a pharmaceutically-acceptable salt thereof, or an eight to eighteen carbon atom inclusive fatty alcohol sulphate, fatty alcohol phosphate, fatty alcohol ether phosphate, fatty alcohol ether sulphate, alkane sulphonate, olefinic sulphonate, sulphocarboxylic acid ester or glyceride sulphate, or a pharmaceutically-acceptable salt thereof.

6. Composition of claim 2, wherein the adjuvant compound is a naturally-occurring fatty acid or a fatty alcohol sulphate with about eight to eighteen carbon atoms, inclusive, or a pharmaceutically-acceptable salt thereof.

7. Composition of claim 2, wherein the adjuvant compound is anionic and contains about eight to twenty-four, carbon atoms inclusive.

8. Composition of claim 2, wherein the xanthate is a compound of formula I, wherein $R^1$ represents benzyl, cyclohexyl, tricyclodecyl, 1-norbornyl, cyclododecyl, n-dodecyl, or 4-isobornylcyclohexyl, and wherein $R^2$ represents sodium or potassium, or $C_1$–$C_4$-alkyl, and, as 4-alkyl, and, as adjuvant compound, a naturally-occurring fatty acid or a fatty alcohol sulphate with eight to fourteen carbon atoms, inclusive, or an alkali metal salt thereof.

9. Composition of claim 2, wherein the xanthate is sodium or potassium-benzylxanthate, sodium or potassium-cyclohexylxanthate, sodium or potassium-1-adamantylxanthate, sodium or potassium-8(9)-tricyclo-[5-2.1.0$^{2.6}$]-decylxanthate sodium or potassium-2-endo or exo-bicyclo[2.2.1$^{1.4}$]-heptyl-xanthate, sodium or potassium-cyclododecylxanthate, sodium or potassiumn-dodecylxanthate, or sodium or potassium-4-isobornyl-cyclohexylxanthate, and wherein the adjuvant compound is an aliphatic monocarboxylic acid having nine to thirteen carbon atoms, inclusive, or a sodium or potassium salt thereof, or a fatty alcohol ether sulphate, phosphate, or phosphonate with eight to eighteen carbon atoms, inclusive, or the sodium or potassium salt thereof, or an alkali metal deoxycholate.

10. Composition of claim 9, wherein the adjuvant compound is the sodium or potassium salt of decanoic acid, undecanoic acid, dodecanoic acid, deoxycholic acid, dodecyl sulfate, or dodecylphosphonic acid.

11. Composition of claim 1, wherein the mole ratio of the xanthate to the adjuvant compound is on the order of 1:6 to 1:0.25.

12. Composition of claim 1, in topical, oral, or parenteral application form.

13. A composition of any of claims 1, 2, 8, 9, 10, and 11, wherein a growth promoter is included in the composition.

14. A composition of claim 13, wherein the growth promoter is insulin.

15. Composition of claim 7, wherein the adjuvant compound contains eight to fourteen carbon atoms inclusive.

16. Composition of claim 11, wherein the ratio of the xanthate to the adjuvant compound is on the order of 1:3 to 1:0.5.

17. Composition of claim 11, wherein the ratio of the xanthate to the adjuvant compound is on the order of 1:1 to 1:2.

18. Composition of claim 12, wherein the composition is in the form of an ointment, gel, spray, tablet, capsule, suppository, infusion solution, or injectable solution.

19. In a method of combating a virus or tumor which comprises administering to a subject or situs afflicted with a virus or tumor, which is susceptible to treatment with a chemotherapeutic agent, an amount of a known antiviral and antitumor xanthate, the improvement comprising administering same together with an activity-enhancing amount of an ionic adjuvant compound containing both a lipophilic group and a hydrophilic group.

20. Method of claim 19, wherein the adjuvant is an anionic adjuvant,

21. A method of claim 19 or 20, wherein a growth promoter is concurrently administered.

22. A method of claim 21, wherein the growth promoter is insulin.

23. A method of claim 19, wherein the composition administered is a composition of claim 2.

24. A method of claim 20, wherein the composition administered is a composition of claim 8.

* * * * *

UNITED STATES PATENT AND TRADEMARK OFFICE
CERTIFICATE OF CORRECTION

PATENT NO. : 4,851,435
DATED : July 25, 1989
INVENTOR(S) : Gerhard Sauer, Eberhard Amtmann, Klaus W. Hummel It is certified that error appears in the above-identified patent and that said Letters Patent is hereby corrected as shown below:

Col. 4, lines 46-47; delete "antitumor composition having enhanced antiviral and antitumor"

Col. 11, line 58; "does" should read -- dose --

Col. 12, line 9; "tomors" should read -- tumors --

Col. 14, line 31; "◻0 1" should read -- ◻0:1 --

Col. 15, line 60; "(=" should read -- ($\hat{=}$ --

Col. 15, line 65; New paragraph should begin with §

Col. 17, line 25; "phythoemogylutinine" should read --phythaemagglutinine--

Col. 19, line 15; "k37" should read -- K37 --

Col. 19, line 30; delete "increasing"

Col. 19, line 64; "potintieting" should read -- potentiating --

Col. 20, line 58; delete "4-alkyl, and, as"

Signed and Sealed this

Nineteenth Day of June, 1990

Attest:

HARRY F. MANBECK, JR.

Attesting Officer

Commissioner of Patents and Trademarks